United States Patent
Job

(10) Patent No.: US 8,562,677 B2
(45) Date of Patent: *Oct. 22, 2013

(54) SPRAY METHOD FOR FORMING SHELLS FOR PROSTHESES

(75) Inventor: Keith Job, Colleyville, TX (US)

(73) Assignee: Mentor Worldwide LLC, Santa Barbara, CA (US)

( * ) Notice: Subject to any disclaimer, the term of this patent is extended or adjusted under 35 U.S.C. 154(b) by 337 days.

This patent is subject to a terminal disclaimer.

(21) Appl. No.: 12/720,715

(22) Filed: Mar. 10, 2010

(65) Prior Publication Data

US 2010/0168853 A1    Jul. 1, 2010

Related U.S. Application Data

(62) Division of application No. 10/918,277, filed on Aug. 13, 2004, now Pat. No. 7,758,788.

(51) Int. Cl.
*A61F 2/12* (2006.01)
*B29C 45/14* (2006.01)

(52) U.S. Cl.
USPC .............................................. 623/7; 264/265

(58) Field of Classification Search
USPC .................................. 623/7–8; 264/255–265
See application file for complete search history.

(56) References Cited

U.S. PATENT DOCUMENTS

| | | |
|---|---|---|
| 3,094,704 A | 6/1963 | Abildgaard |
| 3,094,804 A | 6/1963 | Abildgaard |
| 4,761,299 A | 8/1988 | Hufstetler et al. |
| 4,822,549 A | 4/1989 | Verwilst et al. |
| 4,946,464 A | 8/1990 | Pevsner |
| 4,955,909 A | 9/1990 | Ersek et al. |
| 4,960,425 A | 10/1990 | Yan et al. |
| 5,022,942 A | 6/1991 | Yan et al. |
| 5,064,119 A | 11/1991 | Mellette |
| 5,296,069 A | 3/1994 | Robert |
| 5,525,275 A | 6/1996 | Iversen et al. |
| 5,630,844 A | 5/1997 | Dogan et al. |
| 5,935,164 A | 8/1999 | Iversen |
| 5,961,552 A | 10/1999 | Iversen et al. |
| 5,964,803 A | 10/1999 | Iversen et al. |
| 6,056,993 A | 5/2000 | Leidner et al. |
| 6,605,116 B2 | 8/2003 | Falcon et al. |
| 6,692,527 B1* | 2/2004 | Bellin et al. ...................... 623/8 |
| 6,784,222 B2 | 8/2004 | Zychowski et al. |
| 7,645,475 B2* | 1/2010 | Prewett ....................... 427/2.24 |
| 7,758,788 B2* | 7/2010 | Job ............................... 264/255 |
| 2002/0136907 A1 | 9/2002 | Weber et al. |
| 2002/0143396 A1 | 10/2002 | Falcon et al. |
| 2003/0059599 A1 | 3/2003 | Beckley et al. |
| 2003/0197311 A1 | 10/2003 | Stephenson et al. |
| 2004/0010225 A1* | 1/2004 | Schuessler ................. 604/96.01 |
| 2004/0254545 A1 | 12/2004 | Rider, II et al. |
| 2005/0216094 A1 | 9/2005 | Prewett |
| 2008/0181981 A1* | 7/2008 | Schuessler .................... 425/447 |
| 2008/0275544 A1* | 11/2008 | Berg et al. .................... 623/1.42 |

FOREIGN PATENT DOCUMENTS

| | | |
|---|---|---|
| EP | 0416846 | 9/1990 |
| WO | WO 96/40004 | 12/1996 |
| WO | WO 98/25747 | 6/1998 |

* cited by examiner

*Primary Examiner* — Suzette J Gherbi

(57) ABSTRACT

Shells for mammary prostheses and other devices are created by spraying a silicone dispersion onto a mandrel. Several coats of dispersion are applied with an interval for evaporation of solvent between application of coats. The shells created are uniform in thickness and have a desirably defect-free surface.

14 Claims, 1 Drawing Sheet

SPRAY METHOD FOR FORMING SHELLS FOR PROSTHESES

CROSS-REFERENCE TO RELATED APPLICATION

This application is a divisional of U.S. application Ser. No. 10/918,277, filed on Aug. 13, 2004 now U.S. Pat. No. 7,758,788.

TECHNICAL FIELD

This invention relates to devices that are implantable in the human body such as prostheses and tissue expanders.

BACKGROUND

Implantable prostheses are commonly used to replace or augment body tissue. Such prosthesis include a shell formed of an elastomeric material, e.g., silicone. The shell is filled with filling material such as saline or some other liquid or a gel. The filling of the shell commonly takes place after the shell is inserted through an incision. The shell includes a valve that can accept a filling tube that passes through the incision and is used to fill the shell with a suitable liquid or gel. Once the shell is filled to the desired degree, the filling tube is removed and the incision is closed.

In the case of the female breast, it sometimes necessary to remove some or all of the mammary gland and surrounding tissue in order to treat breast cancer. This surgery leaves a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures.

Implantable prostheses are also used more generally for restoring the normal appearance of soft tissue in various areas of the body.

Tissue expanders generally resemble implantable prostheses except that they include a means for adding additional liquid or gel after the device had been inserted under the skin and the incision has been closed. After implantation the shell is gradually inflated using a liquid or gel, usually over a period of weeks, in order to expand the overlying skin either so that a prosthesis can later be inserted or so that skin can be generated for grafting. The liquid or gel is usually introduced by means of a needle that pierces the skin and a self-seal valve that is integral to the shell or that is remote from the shell and connected to the shell by tubing.

Silicone shells for implantable prosthesis and tissue expanders are generally formed by dipping a suitably shaped mandrel into a silicone dispersion. The mandrel is withdrawn from the dispersion and the excess silicone dispersion is allowed to drain from the mandrel. After the excess dispersion has drained from the mandrel at least a portion of the solvent is allowed to evaporate to stabilize the silicone coating. The process is then repeated one or more times until a shell of the desired thickness is formed. Because the flow of the silicone dispersion as it drains from the mandrel depends on the shape and orientation of the mandrel, the resulting shell can vary substantially in thickness. In addition, because dip casting requires a relatively large vat of silicone dispersion and because solvent evaporates from the silicone dispersion in the vat during the casting process, considerable silicone dispersion waste is created during dip casting.

SUMMARY

The invention features methods for forming the shell of a body implant (e.g., a prosthesis or tissue expander). The methods can also be used to make other articles formed from an elastomeric material (e.g., a patch for an implant) and for applying a coating of an elastomeric material (e.g., silicone) to a device to be implanted into the body (e.g., a pacemaker or implantable pump). The methods of the invention entail spraying a silicone dispersion onto a mandrel or other object. The silicone dispersion is sprayed using, for example, a high volume, low pressure (HVLP) spray device or a rotary atomizer or some other device that sprays the silicone dispersion at a low pressure. The methods described herein can be used, for example, to create an implant shell that is both thinner and more uniform in thickness than that which can be formed using traditional dip casting techniques. In addition, the methods of the invention can be used to create a shell that varies in thickness in a controlled manner. Further, the methods of the invention allow the production of shells having complex shapes that cannot be efficiently formed using traditional dip casting methods. Thus, the methods can be used to make generally spherical, cylindrical, rectangular solids, and cubic shell as well as other shapes, including shapes having edges, corners, recessed regions and other complex geometries. Shells created by the methods of the invention have a generally smoother surface than shells created by traditional dip casting methods.

In one aspect the invention features a method comprising: a) providing a mandrel; b) spraying a silicone dispersion onto the mandrel until a desired thickness of silicone dispersion is formed on the mandrel; c) curing the silicone dispersion to form a silicone device; and d) removing the silicone device from the mandrel. In various embodiments: the silicone dispersion comprises high temperature vulcanization (HTV) silicone, the silicone dispersion comprises room temperature vulcanization (RTV) silicone.

In one aspect the invention features a method for creating a silicone shell, the method comprising: a) providing a mandrel; b) applying a coating silicone dispersion to the mandrel by spraying the silicon dispersion at low pressure; c) allowing evaporation of at least a portion of the solvent in the coating silicone dispersion; d) repeating steps b) and c) until a silicone shell having a desired thickness is formed; e) at least partially curing the silicone shell; and f) removing the silicone shell from the mandrel.

In various embodiments: the silicone dispersion is sprayed onto the mandrel using a high volume low pressure spray device; the silicone dispersion is sprayed onto the mandrel using a rotary atomizer; the silicone dispersion is an HTV silicone dispersion; the silicone dispersion is an RTV silicone dispersion; at least two coats of dispersion are applied to the mandrel; at least three coats of dispersion are applied to the mandrel; at least four coats of dispersion are applied to the mandrel; at least five coats of dispersion are applied to the mandrel; at least six coats of dispersion are applied to the mandrel; the dispersion is sprayed by atomizing the dispersion using a flow of air below 20 psi; the dispersion is sprayed by atomizing the dispersion using a flow of air below 10 psi; the shell is 0.00±0.004" thick; the shell is 0.012"±0.004" thick; the shell is 0.014±0.004" thick; and the shell is 0.013"±0.004" thick.

In other embodiments, the method further comprising applying a coat of silicone dispersion to a portion of the mandrel to create a partial coat of dispersion; the mandrel includes an anterior surface and a posterior surface that meet at a perimeter region; the partial coat of dispersion is applied to the perimeter region of the mandrel; the mandrel has at least one relatively planar region and at least on region that is curved; the partial coat of dispersion is applied to the at least one region that is curved; the mandrel has a first region having a first radius of curvature and a second region having a second smaller radius of curvature; the region having the partial coat of dispersion is applied to the region having a second, smaller radius of curvature; and at least one partial coat of dispersion is applied to at least a first portion of the mandrel.

The invention also features a shell for a tissue expander formed by above-described method and a shell for an implantable prosthesis made by the above-described method.

The invention also features a prosthesis formed by a method comprising providing a shell formed by the above-described method and sealing the shell or sealing the shell while providing the shell with a filling port.

For RTV silicone the silicone dispersion comprises 20-70% silicone solids, 20-60% silicone solids, 20-50% silicone solids, 25-45% silicone solids, 28-40% silicone solids, 28-39% silicone solids, 28-38% silicone solids, 28-36% silicone solids, or 28-34% silicone solids. In certain embodiments the RTV dispersion contains 30-35% solids, preferably 31%+/−3% silicone solids, 31%+/−2% silicone solids, or 31%+/−1% silicone solids. In some embodiments the dispersion contains xylene or another suitable solvent.

For HTV silicone the silicone dispersion comprises 20-70% silicone solids, 20-60% silicone solids, 20-50% silicone solids, 25-45% silicone solids, 30-38% silicone solids, or 32-36% silicone solids. In certain embodiments the HTV dispersion contains 34%30 /−3% silicone solids, 34%+/−2% silicone solids, or 34%+/−1% silicone solids. In some embodiments the dispersion contains xylene or another suitable solvent.

For products filled with saline, the shell is formed of RTV silicone in some embodiments and is formed using a dispersion having a viscosity of 700 to 820 centipoise. For products filled with silicone gel, the shell is formed of HTV silicone in some embodiments and is formed using a dispersion having a viscosity of 500 to 600 centipoise.

The invention also features a silicone device formed by: a) providing a mandrel; b) spraying a silicone dispersion onto the mandrel until a coating of the desired thickness is formed on the mandrel; c) curing the coating of silicone dispersion on; and d) removing the silicone device from the mandrel.

The method can be used to form an HTV silicone shell with a thickness of: 0.013"±0.007", ±0.006", ±0.005", ±0.004", ±0.003", ±0.0025" or ±0.002"; 0.012"±0.007", ±0.006", ±0.005", ±0.004", ±0.003", ±0.0025" or ±0.002"; 0.011"±0.007", ±0.006", ±0.005", ±0.004", ±0.003", ±0.0025" or ±0.002"; 0.010"±0.007", ±0.006", ±0.005", ±0.004", ±0.003", ±0.0025" or ±0.002"; or 0.009"±0.007", ±0.006", ±0.005", ±0.004", ±0.003", ±0.0025" or ±0.002". In certain embodiments the method is used to create a silicone shell that varies in thickness by no more than 0.006", 0.005", 0.004", 0.003", 0.0025" or 0.002".

The method of the invention is used to form an RTV shell with a thickness of: 0.015"±0.007", ±0.006", ±0.005", ±0.004", ±0.003", ±0.0025" or ±0.002"; 0.014"±0.007", ±0.006", ±0.005", ±0.004", ±0.003", ±0.0025" or ±0.002"; 0.013"±0.007", ±0.006", ±0.005", ±0.004", ±0.003", ±0.0025" or ±0.002"; 0.012"±0.007", ±0.006", ±0.005", ±0.004", ±0.003", ±0.0025" or ±0.002"; 0.011"±0.007", ±0.006", ±0.005", ±0.004", ±0.003", ±0.0025" or ±0.002"; 0.010"±0.007", ±0.006", ±0.005", ±0.004", ±0.003", ±0.0025" or ±0.002"; or 0.009"±0.007", ±0.006", ±0.005", ±0.004", ±0.003", ±0.0025" or ±0.002". In certain embodiments the method is used to create a silicone shell that varies in thickness by no more than 0.006", 0.005", 0.004", 0.003", 0.0025" or 0.002".

In some embodiments the mandrel is sprayed with 3, 4, 5, 6, 7 or more coats of silicone dispersion. In some embodiments solvent is allowed to evaporate from the dispersion for 1, 2, 3, 4, 5, 10, 15, 20 or more minutes between coats. In some embodiments the mandrel is rotated during application of the one or more coats of silicone dispersion.

In certain embodiments the first coat of dispersion on the mandrel contains less dispersion than subsequent coats. For example, the first coat is formed by two passes of the spray head over each portion of the mandrel and subsequent coats are formed by three passes of the spray head over each portion of the mandrel. Thus, the first coat contains less material that subsequent coats and is generally thinner than subsequent coats.

The details of one or more embodiments of the invention are set forth in the accompanying drawings and the description below. Other features, objects, and advantages of the invention will be apparent from the description and drawings, and from the claims.

DETAILED DESCRIPTION

Described below are methods for forming a silicone articles, e.g., a shell for soft tissue prostheses. The methods entail spraying a silicone dispersion onto a suitably shaped mandrel or an object to be coated using, for example, a high volume, low pressure (HVLP) spray device or a rotary atomizer. The methods of the invention allow one to control the thickness of shell, permitting the creation of shells that are of a uniform thickness as well as shells that vary in thickness in a controlled manner.

The spraying of the silicone dispersion can be accomplished using HVLP systems. The spraying can be accomplished by atomizing the dispersion using relatively low pressure air. The spraying can also be accomplished by rotary atomization. In rotary atomization the dispersion is feed to a cone or bell spinning at, e.g., 10,000-40,000 RPM. The dispersion is feed to the cone or bell at low pressure (e.g., the dispersion pressure is at or below 30 psi, below 20 psi, 10±4 psi or between 0.1 and 10 psi). Rotary atomization forms a very smooth, uniform layer of silicone that has very few pits or other imperfections. Rotary atomizers are described well known in the art (see, e.g., U.S. Pat. Nos. 5,633,306 and 4,887,770). Rotary atomizers are available from Ransburg Corporation (Toledo, Ohio) and other suppliers. The spray head (cone or bell) of a rotary atomizer can be controlled by a programmable computer so that the spray head makes the same number of passes over all portions of the mandrel or so that the spray head makes more passes over some portions of the mandrel than other portions.

The methods of the invention have numerous advantages over the traditional dip casting technique used to create shells for soft tissue implants. In dip casting, a shell is formed by first dipping a mandrel into a silicone dispersion. Once the mandrel is removed from the dispersion, excess dispersion is allowed to drain from the mandrel. Solvent is allowed to evaporate from the coating of silicone dispersion remaining on the mandrel until the coating is sufficiently stabilized to allow the mandrel to be dipped into the dispersion again. This process is repeated until a shell of the desired thickness is created. Because the flow of the silicone dispersion as it drains from the mandrel depends on the shape and orientation of the mandrel, the resulting shell can vary substantially in thickness. For example, the thickness of the shell of a mammary prosthesis formed by dip casting might vary from 0.009 to 0.024" from one region to another, a variation of more than 100%. Importantly, the thickness of the various regions of the shell is dictated for the most part by the shape of the mandrel and the orientation of the mandrel during the period that the silicone dispersion is draining from the mandrel.

Figure 1:
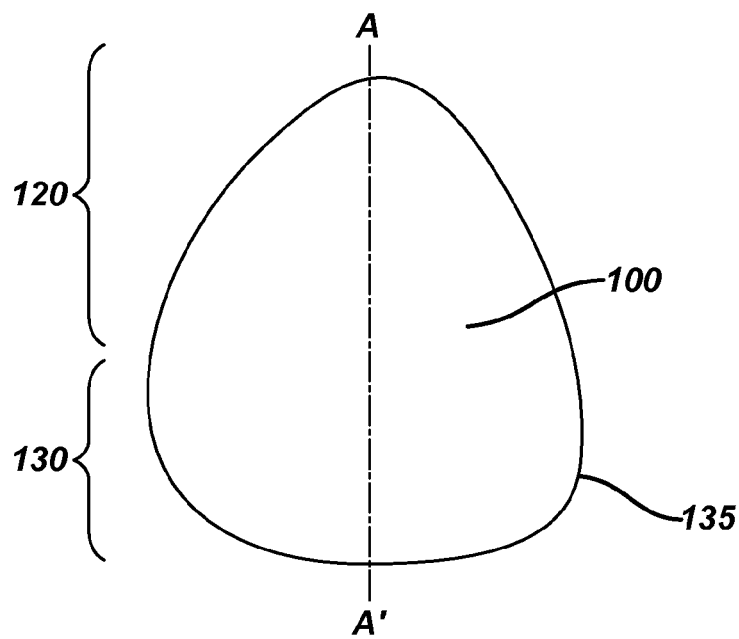
FIG. 1 is a plan view of the anterior face of the shell of a mammary prothesis.
Figure 2:
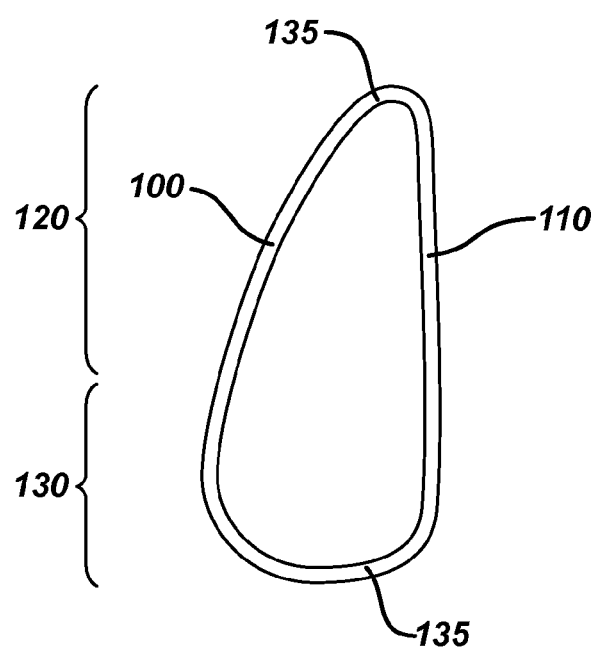
FIG. 2 is schematic drawing of a cross-section of the shell of a mammary prosthesis taken along A-A' in FIG. 1.

FIG. 1 is a plan view of a mammary prosthesis. The anterior face 100 is the outward face when the prosthesis is inserted under the skin of a patient's chest. The prosthesis includes an upper pole region 120 (i.e., the upper half of the shell when the prosthesis recipient is standing) and a lower pole region 130 (i.e., the lower half of the shell when the prosthesis recipient is standing). The region 135 where the anterior face 100 meets the posterior face (not shown) is sometime referred to as the radius, perimeter or edge FIG. 2 is a cross-sectional view of a mammary prosthesis taken along A-A' in FIG. 1. This type of shell has a shape that resembles that of a human breast in that it is fuller in the lower portion than in the upper portion. The shell has an anterior face region 100, a posterior face region 110 (i.e., the face placed against the patient's chest wall when the prosthesis is implanted), an upper pole region 120 and a lower pole region. The region where the posterior and anterior face or surface meet 135, sometimes referred to as the radius, perimeter or edge, is relatively curved compared to the posterior face and to some extent even the anterior face. In the shell depicted here, the radius of curvature of the perimeter in the upper pole region is relatively small. The radius of curvature of the perimeter in the lower pole region is larger. As noted above the shell depicted in FIG. 2 has a shape that more closely resembles the human breast than other types of shells, e.g., shells that are symmetrically dome shaped.

In dip casting the mandrel is held such that the portion corresponding to the anterior face of the shell faces downward. The bracket or rod used to hold the mandrel as it is dipped into the dispersion extends outward from that portion of the mandrel corresponding to the posterior face of the shell. As dispersion drains from the mandrel after it is withdrawn from the dispersion it can be appreciated that it drains relatively rapidly from the perimeter region. As a result, the shell in the perimeter region tends to be thinner than the shell in the anterior face region. For this reason, additional dips are required to create an adequate shell thickness in the perimeter region. This can result in shell that is thicker than desired in the anterior face region. In addition, because the dispersion flows over the mandrel and onto the portion corresponding to the posterior face of the shell, the posterior face region is generally thicker than the shell anterior face region and can be thicker than desired.

As can be seen, the radius of curvature in upper pole transition region 180 between the anterior face region 100 and posterior face region 110 is quite small. It can be desirable for the shell in this region to be thicker than, for example, the anterior face region 100, which should be relatively thin to preserve a natural appearance when implanted in a patient. The method of the invention allows for creating a thicker shell in upper pole perimeter or radius region while maintaining a thinner shell in other regions, e.g., the anterior face region 100 by simply controlling the spray head to apply additional coats of silicone dispersion in the upper pole perimeter or radius region.

In contrast, the methods of the invention can be used to create a shell for a mammary implant or other that varies in thickness from, e.g., 0.009"±0.003" on the faces (e.g., the anterior and posterior faces) to 0.024"±0.003 on the edges or corners where two or more faces meet. The method can also be used to create shells with greater variation in thickness. Thus, as described in greater detail below, the methods of the invention can also be used to create shells that vary in diameter in a controlled manner, i.e., a manner that is not dictated by the shape of the mandrel.

In one embodiment of the invention, a silicone dispersion is applied to a mandrel using a robotically controlled rotary atomizer spray head. The rotary atomizer can operate electrostatically, wherein there is a difference in electrical potential between the silicone and the mandrel. For example, a charge can be applied to the dispersion and the mandrel can be grounded, such that the atomized silicone dispersion is attracted through electrical forces to the mandrel. The spray head makes one or more (e.g., 1, 2, 3, 4, 5, or more) passes over an area of the mandrel to apply one coat of silicone to the entire mandrel or desired portion thereof. The spray head or the mandrel or both can be moved during the application of a coat of silicone dispersion. A number of coats are applied depending on various factors such as the type of silicone used (HTV or RTV), the percent of silicone solids in the dispersion, and the desired thickness of the shell. Between the application of each coat of silicone dispersion solvent is allowed to evaporate so that the coat of silicone dispersion is at least somewhat stabilized prior to the application of the next coat of silicone dispersion. Thus, there is an interval of several minutes (e.g., 2, 3, 4, 5, 6, 10, 12, 15, 20. 25 minutes or more) between the application of one coat of dispersion (which may require 1, 2, 3, 4 or more passes of the spray head over all or a portion of the mandrel) and the next coat of dispersion. Once the desired number of coats of silicone dispersion have been applied, the shell is allowed to fully cure and it is then removed from the mandrel. Because there is no need for excess dispersion to drain from the mandrel, each coat applied is quite uniform in thickness, i.e., it is not significantly thicker in the posterior face region than it is in the anterior face region.

In applying the dispersion, some portions of the mandrel can receive more coats of dispersion than other portions of the mandrel. For example, in the case of a mammary implant the perimeter region can receive more coats of dispersion than the anterior face. In general it can be desirable to apply more coats of material (resulting in a thicker shell) in those regions that correspond to an edge or corner or that otherwise have a smaller radius of curvature than in those regions that are relatively planar.

To provide shells or other devices with one or more regions that are thicker than one or more other regions, it can be desirable to apply more coats of silicone dispersion to some portions of the mandrel than other portions. Thus, one can apply a partial coat of dispersion, i.e. a coat that does not cover the entire mandrel, but instead covers only portion of the mandrel. Additional partial coats can be applied to the mandrel so that one or more portions of the mandrel have 1, 2, 3, 4 or more additional coats of dispersion compared to other portions of the mandrel. Moreover, additional partial coats can be applied to two or more different regions of the mandrel. Thus, the entire mandrel can receive a total 4 coats of dispersion, one portion can receive a total of 5 coats of dispersion and yet another portion can receive a total of 6 coats of dispersion.

It is desirable to use a silicone dispersion having a defined percent solids so that the thickness of the layer of silicone dispersion applied in each coat is relatively predictable. This is in contrast to traditional dip casting methods in which it is desirable to use a silicone dispersion having a defined viscosity. A silicone dispersion having a defined viscosity is desirable in dip casting because the formation of the shell is highly dependent on the bulk flow characteristics of the silicone dispersion. In many instances the relationship between viscosity and percent solids is not predictable. Thus, for shells produced by spray techniques it is desirable to use a dispersion with a defined percent solids rather than a defined viscosity.

EXAMPLE 1

RTV Silicone Shell

An appropriately shaped mandrel for forming the shell of a mammary prosthesis is arranged approximately 3" to 6" inches from a robotically controlled spray head of rotary atomizer spray device (e.g., the Aerobell RMA-101; ITW Ransburg, Inc.; Toledo Ohio). The mandrel is arranged so that the portion of the mandrel corresponding to the posterior face of the shell is facing downward. The mandrel is held on a rod that extends from the downward facing portion of the mandrel and this rod is arranged so as to allow the mandrel to be rotated on the axis of the rod. The mandrel and the spray head are contained in a cabinet where the air temperature is held at 90° F.±10° F. and about 35-45% relative humidity. A RTV silicone dispersion having 31% (±2%) solids in a xylene dispersion is applied to the mandrel using a spray head that travels in an arc from above the mandrel (90° above the horizontal) to below the mandrel (90° below horizontal) completing one pass from above the mandrel (the portion of the mandrel corresponding to the anterior face of the shell) to below the mandrel (the portion of the mandrel corresponding to the posterior face of the shell) in about 5 seconds as the mandrel is rotated at about 20 rpm. The spray head is supplied by a ⅜" diameter supply line and the dispersion is pumped through the line at 8-20 p.s.i. The dispersion can be electrically charged and the mandrel grounded in order to electrostatically attract the silicone dispersion to the mandrel. However, since RTV silicone dispersion is not particularly conductive, similar results can be achieved with and without charging the dispersion. To apply one coat, the spray head travels from above the mandrel to below the mandrel and returns to above the mandrel during which time the mandrel rotates about 5 full revolutions. The application of a single coat of dispersion takes about 15 seconds. Solvent is allowed to evaporate from the silicone dispersion coated on the mandrel for 10 to 20 minutes in a devolatilization step. This process is repeated so that 4 to 5 additional coats of dispersion are applied in the same manner with a devolatilization step occurring between each coat. The final thickness of the shell is 0.014"±0.002". The process can be automated by mounting a number of mandrels on a track that passes the mandrels by the spray head. The spray head can move with the line or the line can pause with a mandrel positioned near the spray head. After the final coat has been applied, the shell is cured by placing the coated mandrel in an oven set to 150° F. for at least 20 to 30 minutes. The shell is stripped from the mandrel and can be used in a tissue expander or prosthesis.

EXAMPLE 2

HTV Silicone Shell

An appropriately shaped mandrel for forming the shell of a mammary prosthesis is arranged approximately 3" to 6" inches from a robotically controlled spray head of rotary atomizer spray device (e.g., the Aerobell RMA-101; ITW Ransburg, Inc.; Toledo Ohio). The mandrel is arranged so that the portion of the mandrel corresponding to the posterior face of the shell is facing downward. The mandrel is held on a rod that extends from the downward facing portion of the mandrel and this rod is arranged so as to allow the mandrel to be rotated on the axis of the rod. The mandrel is heated to about 145° F. by an infrared heating device that allows the surrounding air temperature to be significantly lower. The mandrel and the spray head are contained in a cabinet where the air temperature is held at 115° F.±10° F. and about 35-45% relative humidity. A HTV silicone dispersion having 31% (±2%) solids in a xylene dispersion is applied to the mandrel using a spray head that travels in an arc from above the mandrel (90° above the horizontal) to below the mandrel (90° below horizontal) completing one pass from above the mandrel (the portion of the mandrel corresponding to the anterior face of the shell) to below the mandrel (the portion of the mandrel corresponding to the posterior face of the shell) in about 5 seconds as the mandrel is rotated at about 20 rpm. The spray head is supplied by a ⅜" diameter supply line and the dispersion is pumped through the line at 8-20 psi. Shaping air can be employed to shape the stream of silicone dispersion. The dispersion can be electrically charged (e.g., by applying 80,00 to 100,000 volts at low amperage) and the mandrel grounded in order to electrostatically attract the silicone dispersion to the mandrel. Because HTV silicone dispersion is conductive, superior results can be achieved by charging the dispersion. To apply one coat, the spray head travels from above the mandrel to below the mandrel and returns to above the mandrel during which time the mandrel rotates about 5 full revolutions. The application of a single coat of dispersion takes about 15 seconds. Solvent is allowed to evaporate from the silicone dispersion coated on the mandrel for 10 to 20 minutes in a devolatilization step. This process is repeated so that 3 to 4 additional coats of dispersion are applied in the same manner with a devolatilization step occurring between each coat. The final thickness of the shell is 0.012"±0.002". The process can be automated by mounting a number of mandrels on a track that passes the mandrels by the spray head. The spray head can move with the line or the line can pause with a mandrel positioned near the spray head. After the final coat has been applied, the shell is cured by placing the coated mandrel in an oven set to 325° F. for at least 55 to 65 minutes. The shell is stripped from the mandrel and can be used in a tissue expander or prosthesis.

EXAMPLE 3

Textured Shell

A textured shell can be created by applying solid particles of silicone to a shell between coats of silicone dispersion. A shell of the desired thickness is created as described in Example 1 or Example 2. The shell is partially or fully cured by heating. Alternatively, the shell is not cured at all. The tackiness of an uncured or partially cured silicone shell fosters adhesion of the solid particles. Particles of fully cured HTV or RTV silicone having an average diameter of 100 to 600 microns are applied to the surface of the shell, e.g., by dipping the mandrel into a bed of particles or by blowing particles onto the shell. Because the surface of the shell is tacky and because the silicone particles have a static charge, the silicone particles adhere readily. The silicone particles can be applied at a density that allows almost complete coverage of the shell or partial coverage. Thus, the particles can be applied relatively densely so that there is little exposed shell or they can be applied relatively sparsely so that there is considerable exposed shell. In addition the particles can be applied to only a portion of the shell, e.g., the particles can be applied only to the posterior face of the shell. The shell is heated (at 250-325° F. for 30 to 60 minutes in the case of HTV silicone) to partially cure or gel the silicone layer to which the particles are adhered. Particles that do not adhere to the shell are removed by gently blowing air over the surface of the shell. The shell is then sprayed again with a silicone dispersion (e.g., HTV silicone diluted to, e.g., 10 to 13% solids with xylene, toluene, tetrahydeofuran or some other suitable solvent) to apply a particle coating layer that envelops the applied particles. The particle coating layer is partially cured or gelled by, for example, heating the shell to 250-325° F. for 30 to 60 minutes in the case of particles coated with an HTV silicone dispersion. The application of particles, curing, coating with silicone dispersion and curing is repeated two more times for a total of three application of particles and three applications of silicone dispersion. Finally, the shell is fully cured.

Silicone particles can be created, for example, from fully cured silicone that is cryogenically ground to yield particles ranging in size from 100-600 microns in diameter, e.g., 100-200, 200-300, 300-400, 400-500, or 500-600 microns in diameter. For example, ¼ to ½ inch thick silicone sheets can be cryogenically ground to yield suitable particles. In some cases the particles are subsequently size selected, e.g., by sieving, such that the particles have a selected average size, e.g., 200-300 microns. In some cases the size selection is limited to removing very small particles and very large particles.

As noted above, the silicone particles can be applied several times. In some cases that average size of the silicone particles applied will vary. Thus, the particles applied in the first application of particles can have a first average size and the particles applied in the second application of particles can have a second average size. If there are is a third applications of particles, the particles in this third application can have a third average particle size. Thus, the particles used in each application can have a different average particle size. In some cases, several of the applications of particles can have the same or very similar average particle size. In some cases a given application of particles can include two different groups of particles, one having a first average particle size and the other having a second, different average particle size.

The surface created on the shell is microporous. There are cavities, overhangs, bridges and passageways. However, because each layer of particles is enveloped in silicone, the surface is relatively smoothly modeled. Because the surface of the shell includes cavities, overhangs and passageways, upon implantation, tissue will grow into the cavities, beneath the overhangs and through the passageways. In this manner, the tissue is engaged with the implant. This engagement secures the implant.

OTHER EMBODIMENTS

A soft tissue prosthesis can have any desired shape, e.g., the shell of the prosthesis can be circular, oval, or crescent shaped. The prosthesis can have a single lumen or multiple lumens. It can be formed of silicone rubber, a laminate of various forms of silicone, silicone copolymers, polyurethane, and various other elastomers in various combinations. Various materials are described in U.S. Pat. Nos. 4,592,755 and 4,205,401.

To form a prosthesis from the shell, e.g., a shell formed of HTV silicone, the opening in the posterior face of the shell is sealed using a patch comprising a vulcanized layer of silicone sheeting and an unvulcanized layer of silicone. The patch is shaped and sized to be somewhat larger than the opening in the posterior face of the shell. The patch is positioned inside the shell such that the unvulcanized layer of the patch faces outward and the perimeter of the patch overlaps the edge of the shell surrounding the opening. The assembly is compressed either between hot platens at, e.g., 325° F. and 60 p.s.i. or platens at room temperature and 60 p.s.i. for about two to three minutes. The patched shell is then cured in an oven at 325° F. for about one half hour to cure fully.

The shell can be filled with a fluid or gel. In addition, an amount of solid material can be combined with the fluid or gel to adjust the density or compressibility of the filling.

Elastomers other than silicone may be used. Thus, the mandrel can be sprayed with a dispersion of any elastomer.

The prosthesis of the invention can be provided as a kit with a shell and a means for filling the shell, e.g., a syringe. The kit can further include an adapter tube for connecting the syringe to the filling port of the shell.

A number of embodiments of the invention have been described. Nevertheless, it will be understood that various modifications may be made without departing from the spirit and scope of the invention.

What is claimed is:

1. A shell for an implantable prosthesis formed by:
 a) providing a mandrel;
 b) applying a silicone dispersion coating having a varying thickness and a concentration of silicone to solvent of greater than 20 percent to the mandrel by spraying the silicone dispersion at a pressure of less than 20 psi;
 c) allowing evaporation of at least a portion of the solvent in the coating silicone dispersion;
 d) repeating steps b) and c) until a silicone shell is formed having a thickness of approximately 0.009+/−0.003 inches on an anterior and posterior face of the shell, and a thickness of approximately 0.024+/−0.003 inches at the perimeter interface where the anterior and posterior faces meet;
 e) at least partially curing the silicone shell; and
 f) removing the silicone shell from the mandrel.

2. The shell according to claim 1, wherein the shell is sized and shaped for use as a mammary prosthesis.

3. The shell according to claim 2, wherein at least a portion of an external surface of the shell is textured.

4. The shell according to claim 3, wherein the shell is sealed.

5. The shell according to claim 1, and further formed by, following the removing step, sealing the shell while providing the shell with a filling port.

6. The shell according to claim 5, wherein the shell is sized and shaped for use as a mammary tissue expander.

7. The shell according to claim 6, wherein at least a portion of an external surface of the shell is textured.

8. A mammary prosthesis formed by:
 a) providing a mandrel;

b) applying a silicone dispersion coating having a concentration of silicone to solvent of greater than 20 percent to the mandrel by spraying the silicone dispersion at pressure of less than 20 psi;
c) allowing evaporation of at least a portion of the solvent in the coating silicone dispersion;
d) repeating steps b) and c) until a silicone shell is formed having a thickness of approximately 0.009+/−0.003 inches on an anterior and posterior face of the shell, and a thickness of approximately 0.024+/−0.003 inches at the perimeter interface where the anterior and posterior faces meet;
e) at least partially curing the silicone shell; and
f) removing the silicone shell from the mandrel.

9. The prosthesis according to claim 8, wherein the prosthesis is adapted to be filled with fluid, and wherein when so filled the prosthesis is sized and shaped for use as a mammary implant.

10. The prosthesis according to claim 9, wherein at least a portion of an external surface of the prosthesis is textured.

11. The prosthesis according to claim 10, wherein the prosthesis is sealed.

12. The prosthesis according to claim 8, and further formed by, following the removing step, sealing the prosthesis while providing the prosthesis with a filling port.

13. The prosthesis according to claim 12, wherein the prosthesis is sized and shaped for use as a mammary implant.

14. The prosthesis according to claim 13, wherein at least a portion of an external surface of the prosthesis is textured.

\* \* \* \* \*